United States Patent
Leong et al.

(10) Patent No.: US 7,969,573 B2
(45) Date of Patent: Jun. 28, 2011

(54) METHOD AND SYSTEM FOR OBTAINING N AND K MAP FOR MEASURING FLY-HEIGHT

(75) Inventors: Siang Huei Leong, Singapore (SG); Zhimin Yuan, Singapore (SG); Bo Liu, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 416 days.

(21) Appl. No.: 12/083,064

(22) PCT Filed: Sep. 27, 2006

(86) PCT No.: PCT/SG2006/000283
§ 371 (c)(1),
(2), (4) Date: Sep. 8, 2008

(87) PCT Pub. No.: WO2007/040462
PCT Pub. Date: Apr. 12, 2007

(65) Prior Publication Data
US 2009/0268323 A1    Oct. 29, 2009

Related U.S. Application Data

(60) Provisional application No. 60/722,978, filed on Oct. 4, 2005.

(51) Int. Cl.
*G01J 4/00* (2006.01)
(52) U.S. Cl. .................................................. 356/369
(58) Field of Classification Search .................. None
See application file for complete search history.

(56) References Cited

U.S. PATENT DOCUMENTS

| | | | |
|---|---|---|---|
| 5,280,340 A | 1/1994 | Lacey | |
| 5,457,534 A | 10/1995 | Lacey et al. | |
| 5,502,565 A | 3/1996 | Fukuzawa et al. | |
| 5,710,632 A | 1/1998 | Li | |
| 5,781,299 A | 7/1998 | Womack et al. | |
| 5,793,480 A | 8/1998 | Lacey et al. | |
| 5,818,592 A * | 10/1998 | Womack et al. | 356/507 |
| 6,665,077 B1 * | 12/2003 | Stirniman et al. | 356/507 |
| 6,804,010 B1 * | 10/2004 | Stirniman | 356/507 |
| 2002/0018214 A1 * | 2/2002 | Liu et al. | 356/507 |

OTHER PUBLICATIONS

"Determining the optical constants of read-write sliders during flying-height testing", Peter de Groot, Ara Dergevorkian, Tod Erickson, and Russell Pavlat, vol. 37, No. 22, p. 5116-5125, Aug. 1, 1998.

(Continued)

*Primary Examiner* — Gregory J Toatley
*Assistant Examiner* — Juan D Valentin
(74) *Attorney, Agent, or Firm* — Harness, Dickey & Pierce, P.L.C.

(57) ABSTRACT

A method for obtaining a refractive index (n) and extinction coefficient (k) map of a slider surface, the method comprising the steps of processing an image of the slider surface to obtain spatially resolved normalized intensity data of the slider surface; measuring n and k values of the slider surface at different areas of the slider surface to obtain reflectivity data of the slider surface; mapping a distribution of the normalized intensity data to a distribution of the reflectivity data for deriving the n and k map of the slider surface.

23 Claims, 10 Drawing Sheets

OTHER PUBLICATIONS

"In-Situ n & k Phase Compensation in an Interferometric Flying Height Tester", Kenneth H. Womack and Allan Butler, IEE Transactions On Magnetics, vol. 34, No. 2, p. 459-461, Mar. 1998.

"Interferometric Measurement of Disk/Slider Spacing: The Effect of Phase Shift on Reflection", Christopher Lacey, Rick Shelor, A.J. Cormier and F.E. Talke, IEEE Transactions On Magnetics, vol. 29, No. 6, p. 3906-3908, Nov. 1993.

"Flying Height Test Considerations", Carlos A. Duran, Phase Metrics, Inc. 1998.

"Error Analysis of a Multiwavelength Dynamic Flying Height Tester", Carlos A. Duran, IEEE Transactions On Magnetics, vol. 32, No. 5, p. 3720-3722, Sep. 1996.

"Optical properties of alumina titanium carbide sliders used in rigid disk drivers", Peter de Groot, Applied Optics, vol. 37, No. 28, p. 6654-6663, Oct. 1, 1998.

"Accurate Flying Height Measurements For Next Generation Sliders", Rui-fang Shi, Carlos A. Duran and Mark Carder, Phase Metrics, Inc., Dec. 1, 1999.

"Normal Incidence Polarization Interferometer for Measuring Flying Height of Magnetic Heads", Xinqun Liu, Warwick Clegg, and Bo Liu, IEEE Transactions On Magnetics, vol. 35, No. 5, p. 2457-2459, Sep. 1999.

\* cited by examiner

METHOD AND SYSTEM FOR OBTAINING N AND K MAP FOR MEASURING FLY-HEIGHT

This application is a 371 National Stage of International application No. PCT/SG2006/000283, filed Sep. 27, 2006 and published in English as WO 2007/040462 A1 on Apr. 12, 2007. This application claims the benefit of U.S. Provisional Application No. 60/722,978, filed Oct. 4, 2005. The disclosures of the above applications are incorporated herein by reference.

FIELD OF INVENTION

The present invention relates broadly to a method and system for obtaining a refractive index (n) and extinction coefficient (k) map of a slider surface, and to a data storage medium having computer code means stored thereon for instructing a computer to execute a method for obtaining a refractive index (n) and extinction coefficient (k) map of a slider surface.

BACKGROUND

For data storage devices such as hard disk drives, taking fly-height (FH) measurements in standard commercial fly-height testers (FHTs) typically requires to first measure optical constants, ie. reflective index (n) and extinction coefficient (k), by using separated equipment such as a spectroscopic ellipsometer.

One problem that may arise is that there is a difficulty to ensure that n and k are measured at the same spot for the ellipsometry measurement and for the FH testing performed after the ellipsometry measurement. Thus, due to potential variation in n and k across a slider surface, errors as large as 1.0 to 2.0 nm may be encountered in FH measurements. This error range is not acceptable since FHs are approaching the sub-10 nm regime due to increases in storage densities of modern hard disk drives.

In addition to the above, the n and k ambiguity typically leads to other problems when load/unload (L/UL) calibration is employed. L/UL calibration is currently recognised as an important step in commercial FH testing as described in U.S. Pat. No. 5,457,534. L/UL calibration is used to identify the maximum and minimum of a FH interferometric signal as a slider is lifted or unloaded from its flying position above a disk surface. Due to the design of current negative pressure sliders, it is typically very difficult to perform L/UL calibration at a slider trailing edge. Thus, if it is derived to measure the FH at the trailing edge, the L/UL calibration has to typically be performed elsewhere on the slider. However, because of the uncertainty in the n and k properties across the slider surface, it is typically not reliably possible to find positions of similar n and k for the L/UL calibration and generally, the FH testing spot.

Furthermore, an inspection of the standard equation for intensity, $I_A$, for thin film interference (see eq. 1) reveals that two parameters dependent on the slider n and k properties are present.

$$I_A = \frac{r_A^2 + r_2^2 + 2r_A r_2 \cos\delta}{1 + r_A^2 r_2^2 + 2r_A r_2 \cos\delta} \quad \text{eq. 1}$$

The two parameters are the reflectance at slider-air interface, $r_A$ and path difference, $\delta$. $\delta$ is a function of fly height, h, incident wavelength, $\lambda$, and phase change on reflection, $\phi_a$, where $\phi_s$ is n, k dependent. Therefore, yet another problem that may arise is that use of inaccurate n and k values results in an inaccurate calculation of the FH, based on interferometric intensity.

Thus, being unable to use similar and accurate n and k values at both the L/UL and FH testing points typically results in a double penalty.

In an attempt to solve the above problems, in-situ n and k compensation has been suggested. In-situ n and k compensation uses a means through which, or a parameter by which, to predict, or measure the local optical properties, namely n and k.

An in-situ n and k compensation method described in IEEE Trans. Magn., 34(2), 459, 1998 by Womack et al. is directed at gauging n and k by means of intensity, where an empirical linear relationship generally exists between calculated reflectivity and ellipsometric measured n and k properties. In Womack et al.'s approach, a glass reference prism is used next to a spinning glass disk to allow a separate measurement of the reflectivity R. However, this direct approach to link R to n and k may give rise to a problem in that the obtained measured intensity contains a component mediated by the interferometric nature of the approach and therefore, does not compute as the intensity that would be obtained by calculations that use the ellipsometrically measured n and k values. It has been observed that with inherent FH information mixed with n and k induced intensity changes, it may not be possible to accurately determine n and k directly by using Womack et al.'s approach. It has been found that the measured intensity is approximately 20% lower than the predicted value based on the n and k model, indicating that the Womack et al.'s direct approach may not be applicable.

Hence, there exists a need for a method and apparatus for measuring FH to address at least one of the above problems.

SUMMARY

In accordance with a first aspect of the present invention, there is provided a method for obtaining a refractive index (n) and extinction coefficient (k) map of a slider surface, the method comprising the steps of processing an image of the slider surface to obtain spatially resolved normalized intensity data of the slider surface; measuring n and k values of the slider surface at different areas of the slider surface to obtain reflectivity data of the slider surface; mapping a distribution of the normalized intensity data to a distribution of the reflectivity data for deriving the n and k map of the slider surface.

A corresponding reflectivity value for each data point of the spatially resolved normalized intensity data may be determined from the mapping of the distributions, a corresponding n value may be derived from the corresponding reflectivity value, and a corresponding k value may be calculated from the corresponding reflectivity and n values.

The corresponding n value may be derived from the corresponding reflectivity value based on an empirical relationship.

The empirical relationship may be based on an empirical linear curve.

Processing the image may comprise removing height related information utilising a plane-fit processing.

The plane-fit processing may comprise determining a plane having a minimum sum of squared distances in a normal direction of the plane.

The processing of the image may comprise removing illumination condition related information utilising a normalization processing.

The normalization processing may comprise dividing the image into tiles and the normalized intensity data may be based on normalizing maximum and minimum pixel values in each tile.

The n and k values may be measured utilising ellipsometry.

The image may comprise a charge-coupled device (CCD) image.

A fly-height measurement of the slider may be performed utilising the n and k map of the slider surface.

In accordance with a second aspect of the present invention, there is provided a system for obtaining a refractive index (n) and extinction coefficient (k) map of a slider surface, the system comprising a processor for processing an image of the slider surface to obtain spatially resolved normalized intensity data of the slider surface; a measurement unit for measuring n and k values of the slider surface at different areas of the slider surface to obtain reflectivity data of the slider surface; a mapping unit for mapping a distribution of the normalized intensity data to a distribution of the reflectivity data for deriving the n and k map of the slider surface.

The mapping unit may determine a corresponding reflectivity value for each data point of the spatially resolved normalized intensity data from the mapping of the distributions, may derive a corresponding n value from the corresponding reflectivity value, and may calculate a corresponding k value from the corresponding reflectivity and n values.

The corresponding n value may be derived from the corresponding reflectivity value based on an empirical relationship.

The empirical relationship may be based on an empirical linear curve.

The processor may remove height related information by utilising a plane-fit processing.

The plane-fit processing may comprise determining a plane having a minimum sum of squared distances in a normal direction of the plane.

The processor may remove illumination condition related information by utilising a normalization processing.

The normalization processing may comprise dividing the image into tiles and the normalized intensity data may be based on normalizing maximum and minimum pixel values in each tile.

The n and k values may be measured by utilising ellipsometry.

The image may comprise a charge-coupled device (CCD) image.

A fly-height measurement of the slider may be performed utilising the n and k map of the slider surface.

In accordance with a third aspect of the present invention, there is provided a data storage medium having computer code means stored thereon for instructing a computer to execute a method for obtaining a refractive index (n) and extinction coefficient (k) map of a slider surface, the method comprising the steps of processing an image of the slider surface to obtain spatially resolved normalized intensity data of the slider surface; measuring n and k values of the slider surface at different areas of the slider surface to obtain reflectivity data of the slider surface; mapping a distribution of the normalized intensity data to a distribution of the reflectivity data for deriving the n and k map of the slider surface.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

In the description below, a broad description of an example implementation is first provided followed by a more detailed description of the example implementation. The example implementation reconciles, by using mapping, n and k related information from a physical flying slider to n and k information from ellipsometric measurements.

Figure 1:
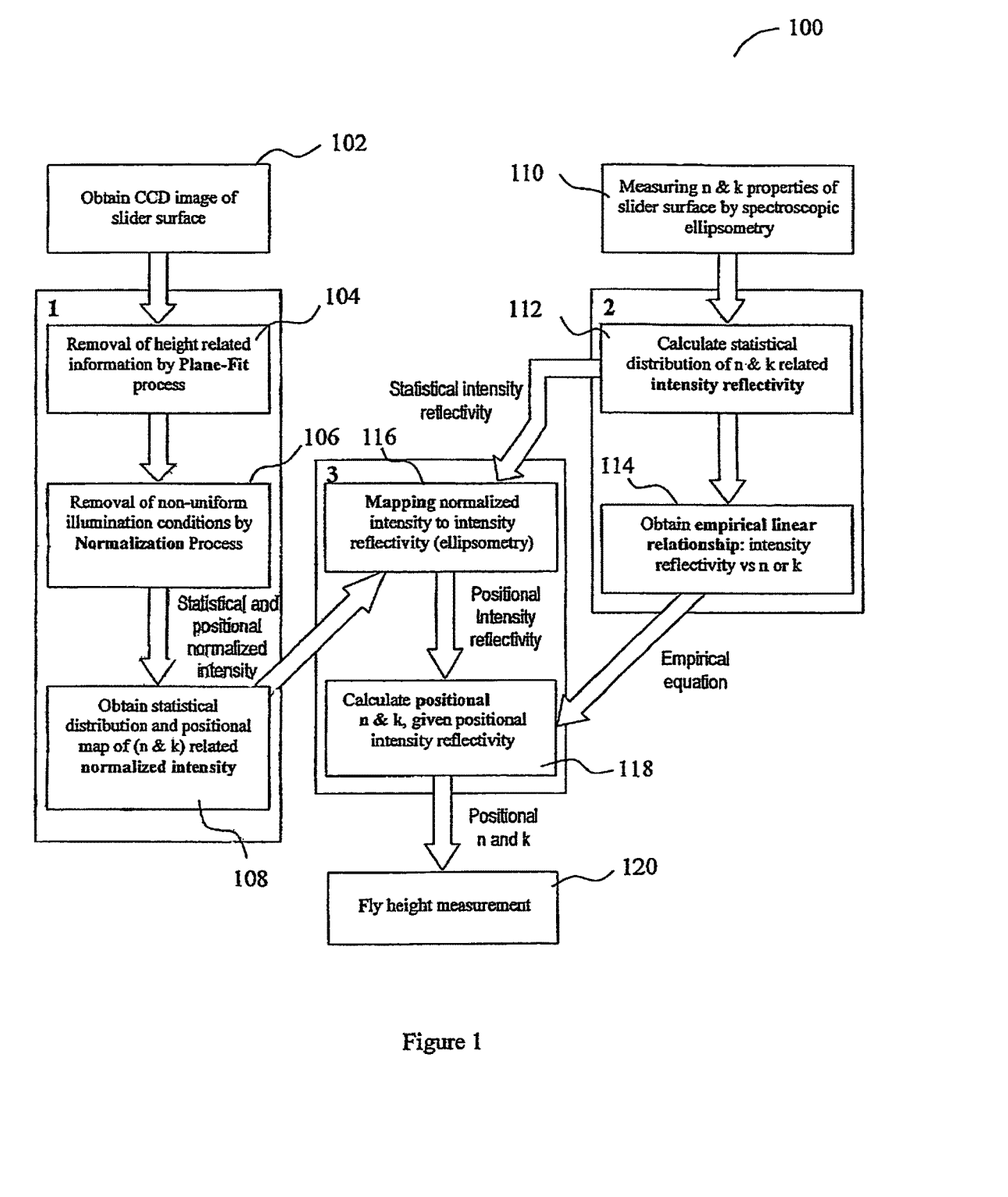
FIG. 1 is a flowchart illustrating the steps of an example implementation.

FIG. 1 is a flowchart 100 illustrating the steps of the example implementation. At step 102, a charge-coupled device (CCD) image of an air bearing surface of a loaded and flying slider is taken through a spinning glass disc. At step 104, height and tilt information, such as pitch and roll induced contrast, are removed from the CCD image using a plane-fit process. At step 106, the CCD image is tiled and contrast from localized non-uniform illumination is removed from the CCD image using a normalization process. At step 108, normalized intensity is calculated for all the tiles and a statistical distribution of the normalized intensity is obtained.

At step 110, n and k measurements of the slider are obtained using ellipsometry. At step 112, intensity reflectivity values are calculated from the n and k measurements and a statistical distribution of intensity reflectivity is generated. At step 114, a linear empirical relationship is obtained between the intensity reflectivity and n.

At step 116, the normalized intensity is statistically mapped to the intensity reflectivity. This mapping is based on the respective statistical distributions in steps 108 and 112. Thus, following step 116, each tile on the slider surface is statistically assigned an intensity reflectivity and a corresponding n value. This assignment is based on the normalized intensity of each tile being mapped to an intensity reflectivity. At step 118, the optical constant k is calculated for each tile based on the statistically assigned intensity reflectivity and corresponding n value. At step 120, FH measurement is performed.

With the positional n and k information from steps 116 and 118 available, the FH measurement using the example implementation is more accurate than for existing techniques.

Following the above broad description, a more detailed description of the example implementation is provided below.

Figure 2:
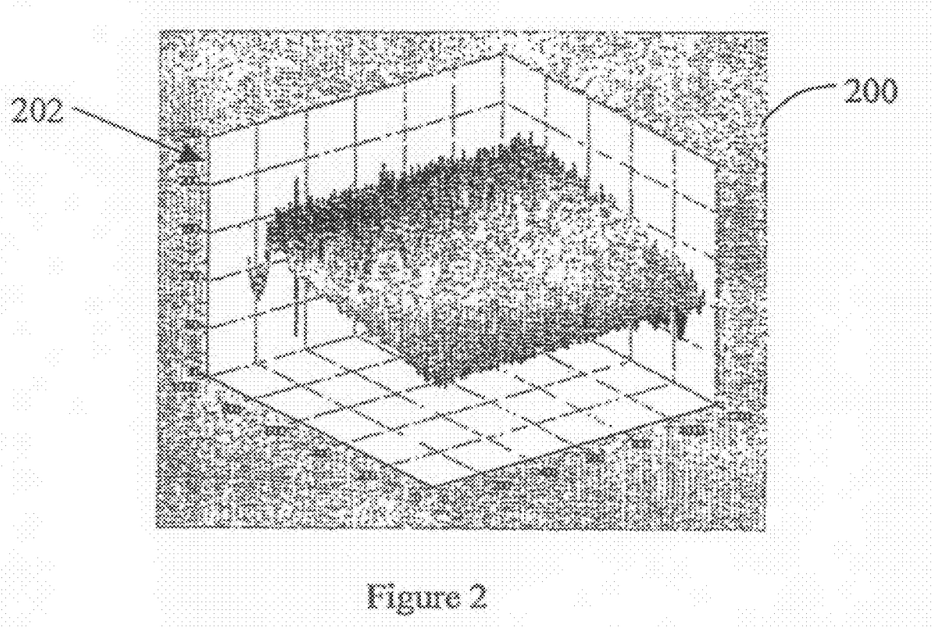
FIG. 2 is a CCD image of a region on a flying slider.

FIG. 2 is a CCD image 200 of a region on a flying slider as taken from a FH tester perspective. From the image 200, it can be seen that the intensity data (see z-axis 202) comprises a flying height dependent component, which reveals that the slider is flying at an angle and is non-parallel to the spinning glass disk.

In the example implementation, a plane fit process is used to remove the effects of 'tilt' or intensity gradient present in the slider intensity image 200. Removing the effects of 'tilt' or intensity gradient can restore the n and k induced reflectivity information, if not at an absolute level, at least at a relative level. At the relative level, a basis for relative comparison of n and k properties between regions on the slider may be provided.

Figure 3:
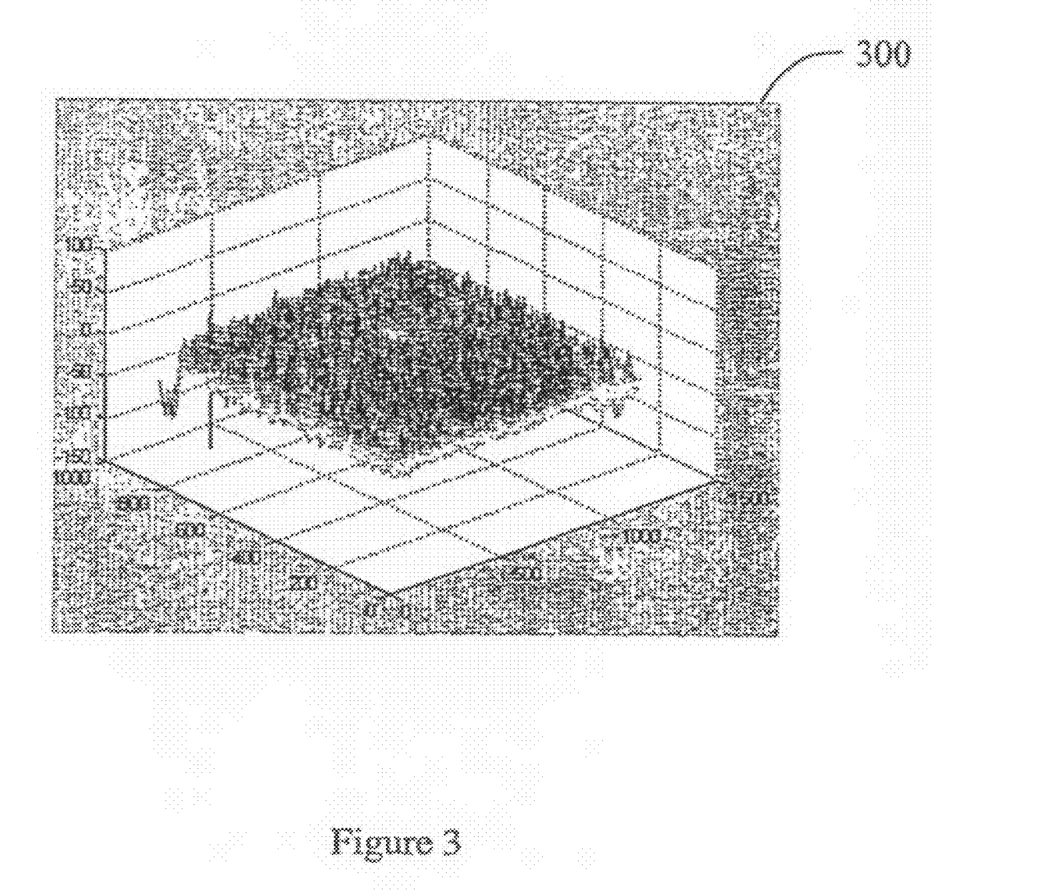
FIG. 3 is a resultant CCD image after a plane fit process is carried out on the CCD image in FIG. 2.

FIG. 3 is a resultant CCD image 300 after a plane fit process is carried out on the CCD image 200 (FIG. 2). The plane fit process is carried out to remove e.g. slider tilt or relative fly-height information across the slider surface.

The plane fit process comprises finding the 'best fit plane' that is the plane that has a minimum sum of squared distances from the plane-to-be-fitted in the z-direction (ie. the normal direction of the plane). In the example implementation, the z-direction refers to the intensity or pixel values in the image 300.

Given that the equation of a plane is $$z = ax + by + c \quad \text{eq. 2}$$

The best fit plane may be found by performing partial differentiation with respect to a, b and c in eq.2 to minimize the sum of squared distances. The following matrix in eq.3 is obtained. $SX_i$, $SY_i$ etc respectively refer to the summation of all X values and Y values in the image, and Z is the pixel value in the image.

$$\begin{bmatrix} N & SX_i & SY_i \\ SX_i & SX_iX_i & SX_iY_i \\ SY_i & SX_iY_i & SY_iY_i \end{bmatrix} \begin{bmatrix} c \\ a \\ b \end{bmatrix} = \begin{bmatrix} SZ_i \\ SX_iZ_i \\ SY_iZ_i \end{bmatrix} \quad \text{eq. 3}$$

The matrix equation eq.3 is solved to obtain values of c, a and b and thus, providing the equation of the best fit plane (see eq.2). After obtaining the equation of the best fit plane, by subtracting from each individual intensity value its best-fit corresponding value, the "flattened" CCD image 300 or map is created from CCD image 200 (FIG. 2).

After the plane fit process, further processing of the CCD intensity information comprises breaking up or dividing the whole image 300 into systematic similar sized squared regions or tiles. Although tilt or relative FH information has been effectively removed from the CCD intensity map after plane-fitting, the resulting intensity map 300 may contain information that is modulated by local variations of illumination and scattering. These effects may exist in terms of the different tiles occupying slightly different CCD pixel ranges and may disallow effective comparison between the various tiles. A normalization process is thus carried out to arrange each tile into a pixel range to enable effective comparison.

Figure 4:
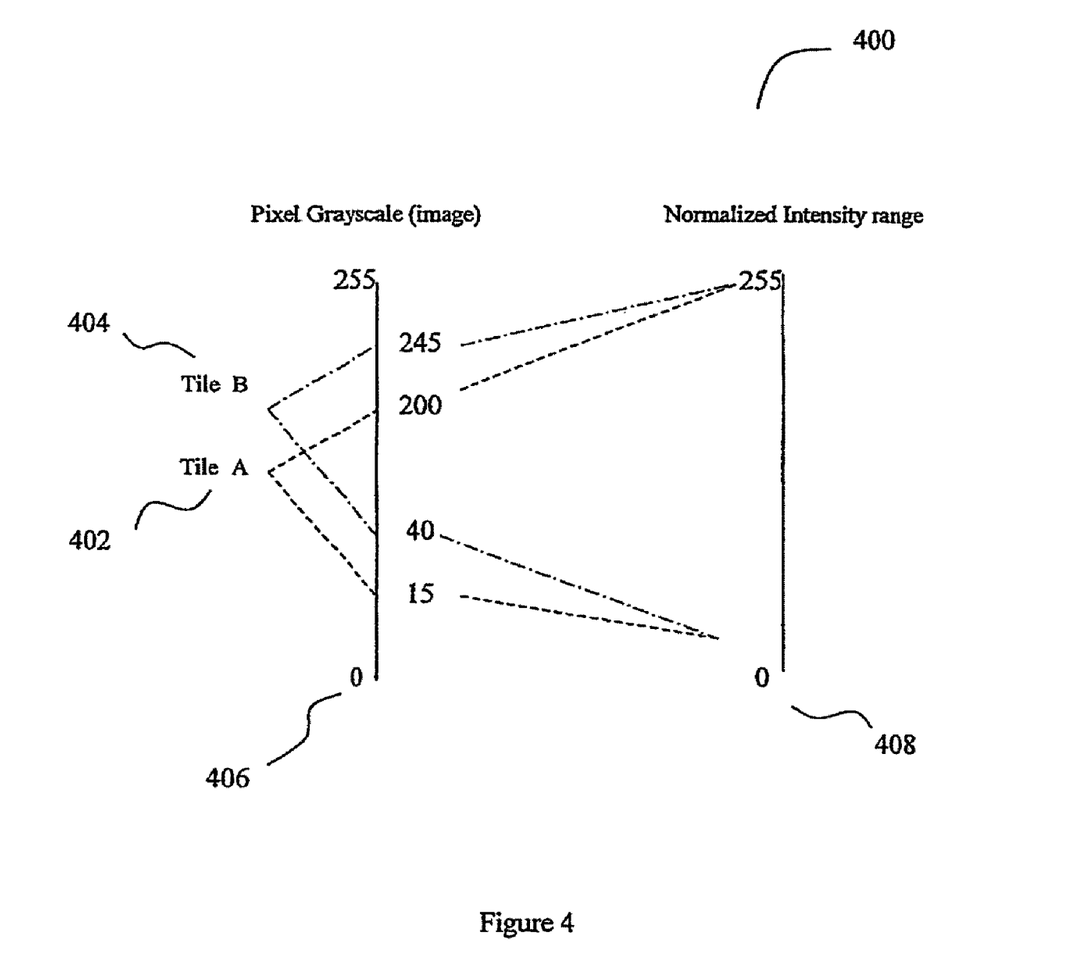
FIG. 4 is a schematic diagram for illustrating a normalization process.

FIG. 4 is a schematic diagram 400 illustrating the normalization process. In the normalization process, tile A 402 and tile B 404 with initially different pixel ranges (see numeral 406) are set to a same normalized range 408. This allows for effective comparison to be carried out.

To set a tile 402 or 404 into the normalized range 408, the largest pixel value $P_{max}$ and the smallest pixel value $P_{min}$ residing within the tile 402 or 404 are determined. Subsequently, each pixel, $P_i$ in the tile 402 or 404 is normalized according to the following eq.4:

$$P_{i(normalized)} = \frac{P_i - P_{min}}{P_{max} - P_{min}} \times 255. \quad \text{eq. 4}$$

The inventors have recognised that establishing a cut-off level for counting statistics in a CCD intensity analysis approach towards estimation of TIC composition on a slider surface is difficult and involves finding a fitting parameter to estimate the composition. An alternative more viable approach comprises noting that the relative contributions of the slider materials in each tile exist in an accumulated intensity value over the each tiled area.

Having performed the normalization process, the summed intensity value over all pixels in each tile provides a representative intensity value hereby termed as accumulated normalized intensity (ANI). This ANI approaches a single intensity value, as with a single detector, that is representative of an average reflectivity across each tiled surface. Thus, comparisons may be made between different tiles based on their respective ANI values. In the example implementation, the size of each tiled area is set to match the size seen by a FH detector.

Figure 5:
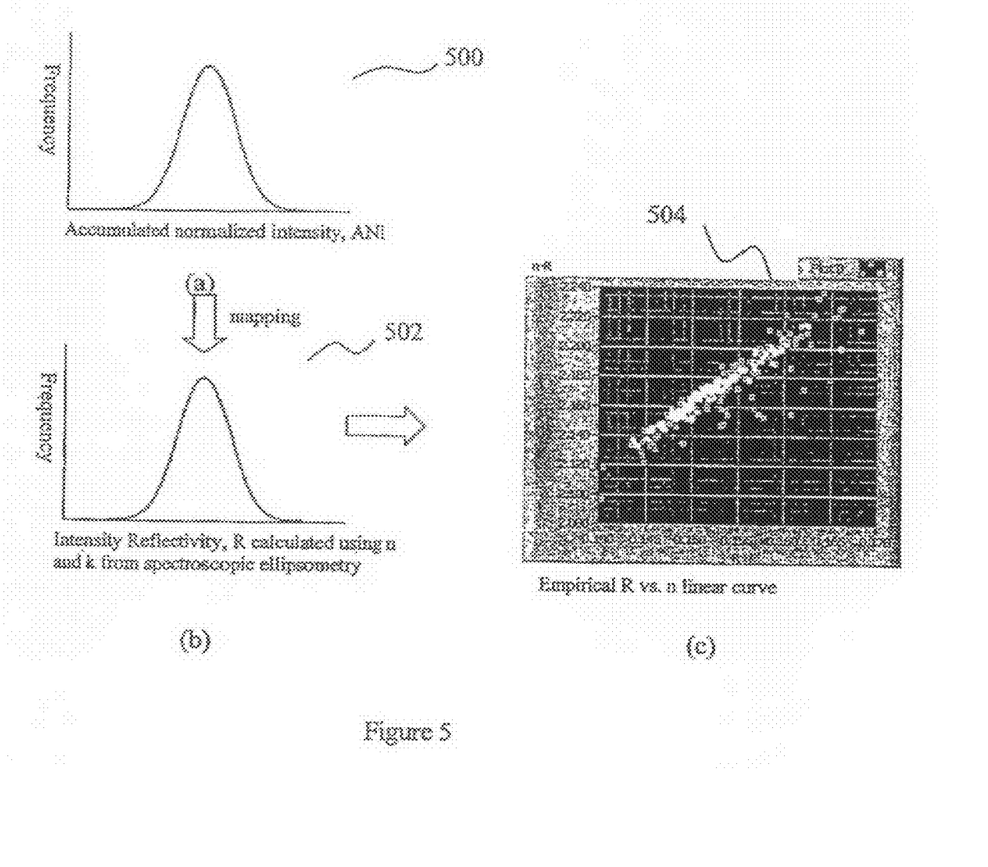
FIG. 5(a) is a graph showing a statistical distribution of accumulated normalised intensity (ANI) values.
FIG. 5(b) is a graph showing a statistical distribution of intensity reflectivity R.
FIG. 5(c) is a graph of reflective index n plotted against intensity reflectivity R.

FIG. 5(a) is a graph 500 showing a statistical distribution of the ANI values. The statistical distribution of the ANI values approaches a Normal/Gaussian distribution and may be analyzed for both its mean and standard deviation.

In the example implementation, intensity values, ie. intensity reflectivity R values, are calculated from n and k measurements, using eq.5 below.

$$R = |(1-n-ik)/(1+n+ik)|^2 \quad \text{eq.5}$$

The n and k measurements are in turn obtained using spectroscopic ellipsometry measurements over a large sample size of the slider surface. It will be appreciated by a person skilled in the art that it is not practical to sample the n and k of the entire slider using ellipsometry although the sample size should ideally be the same as the CCD image (ie. across the entire slider surface). The example implementation works by "extrapolating" statistical information over the entire slider area based on the sample size.

FIG. 5(b) is a graph 502 showing a statistical distribution of the intensity reflectivity R.

FIG. 5(c) is a graph 504 of n (y-axis) plotted against R (x-axis). From graph 504, it is shown that besides giving a normal distribution, the n and k values obtained from ellipsometry measurements also follow an empirical linear relationship that links the calculated intensity reflectivity R to n.

By comparing the two normal distributions of graph 500 and graph 502 arranged side-by-side, a positional mapping of the ANI value of each tile to a corresponding calculated R value is performed. Alternatively, the positional mapping may be performed by aligning graph 500 and graph 502 one over the other. Using the corresponding calculated R value from graph 502 for an ANI value from graph 500, an n value is obtained from the linear empirical curve (graph 504). This is performed for the ANI value of each tile. Using both the R and the n values, k, which is the imaginary part of the refractive index, is calculated. In this fashion, the spatially resolved ANI values represented by the tiles are associated with corresponding R, n, and k values, and thus the spatial information from the image 300 (FIG. 3) is utilised to create an n and k map of the slider surface.

It has been described that spectroscopic ellipsometry measurements over a large sample size of the slider surface are taken. An ellipsometry sample size of 200 or more is used for one slider in the example implementation. It will be appreciated by a person skilled in the art that since material characteristics of sliders in a same lot or batch are statistically similar, the statistics obtained for the one sampled slider may be used for the lot or batch of sliders. The above sample size used may be more than the number of tiles in the CCD image. Thus, the image may be "over-sampled" by using overlapping tiles, if desired, to generate a ANI distribution with a shape that is similar to the shape of the intensity reflectivity distribution. The distributions are then mapped as described above.

Based on the n and k values assigned to each tile, L/UL calibrations may thus be performed at locations with n and k values similar to the n and k values of the desired FH measurement position based on the derived n and k map of the slider surface. In addition, with more accurate n and k values, compared to using averages, the measured FH values can be more accurate and repeatable.

Figure 6:
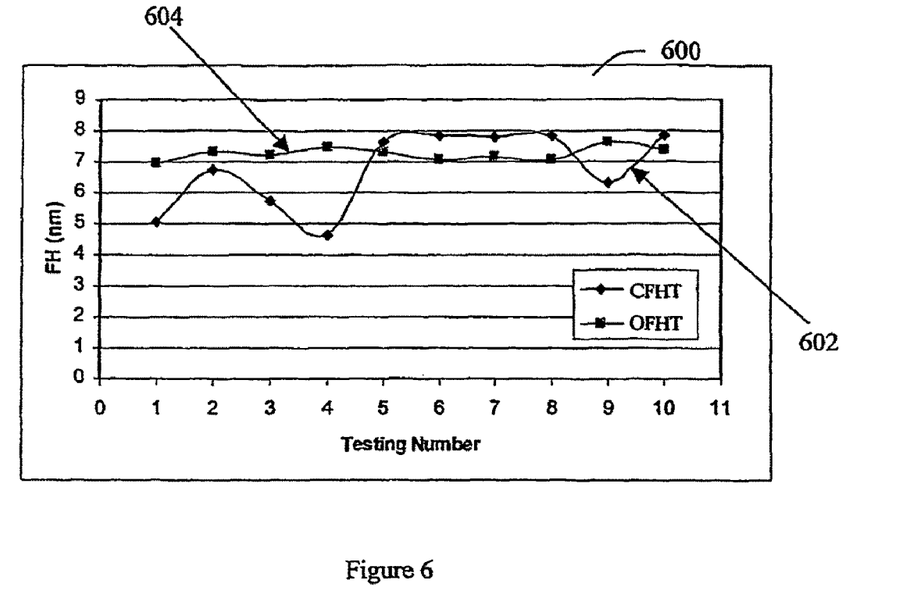
FIG. 6 is a graph of fly-height measurement y-axis) plotted against testing number (x-axis).

FIG. 6 is a graph 600 of FH measurement (y-axis) plotted against testing number (x-axis). On one hand, plot 602 is a plot of FH measurements taken for a slider using a typical commercial FH measurement tool CFHT. An average n and k value is used for the FH measurements since the tool does not provide n and k compensation. On the other hand, plot 604 is a plot of FH measurements taken for the slider using a FH tester OFHT implementing the example implementation, ie. with n and k compensation.

As can be seen from graph 600, the example implementation provides greater FH measurement repeatability. In addition, the standard deviation for the FH measurements taken using the example implementation is smaller (see FH measurement range). This signifies lesser ambiguity in absolute FH measurements.

Figure 7:
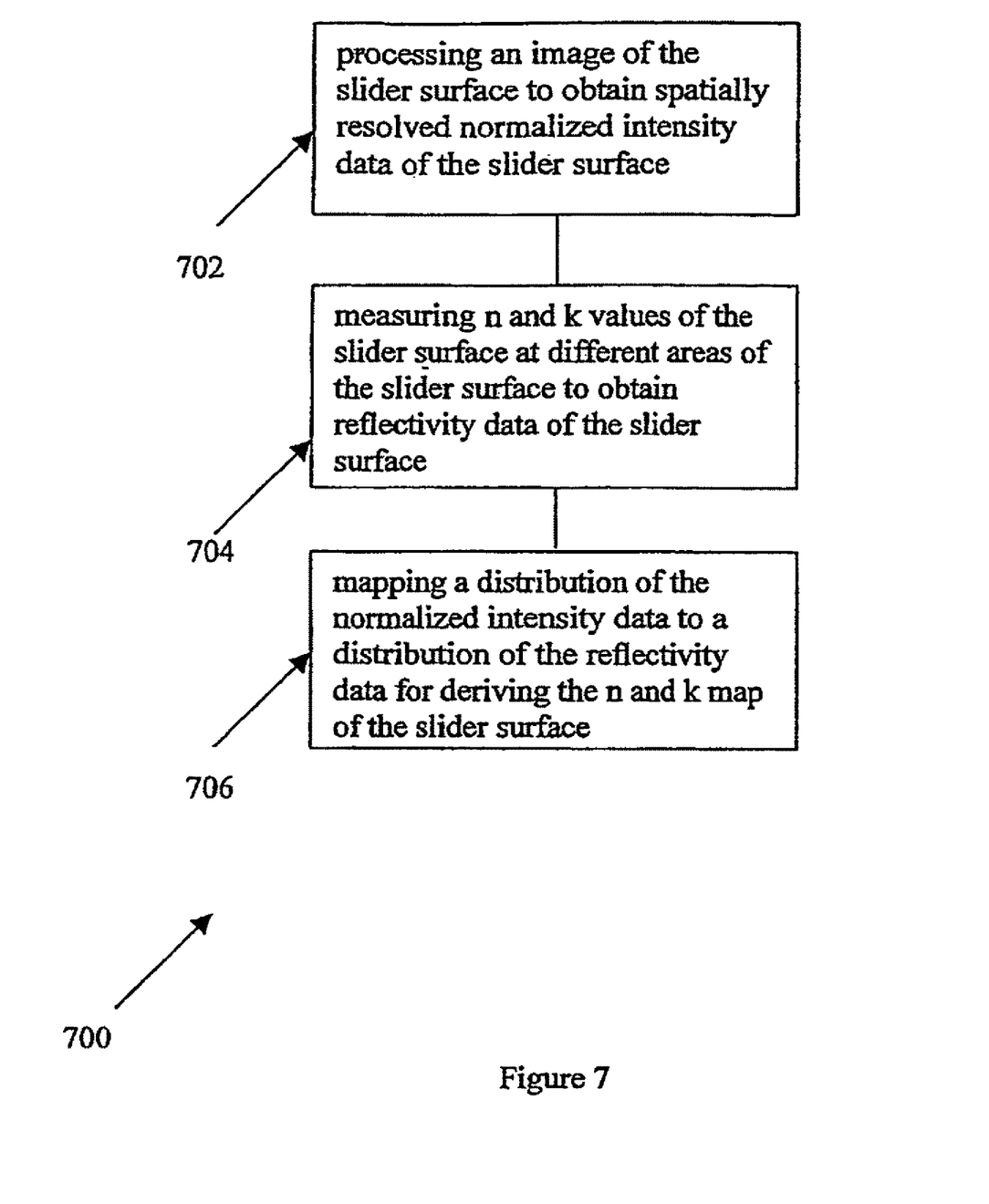
FIG. 7 is a flowchart illustrating a method for obtaining an n and k map of a slider surface.

FIG. 7 is a flowchart 700 illustrating a method for obtaining a refractive index (n) and extinction coefficient (k) map of a slider surface. At step 702, an image of the slider surface is processed to obtain spatially resolved normalized intensity data of the slider surface. At step 704, n and k values of the slider surface are measured at different areas of the slider surface to obtain reflectivity data of the slider surface. At step 706, a distribution of the normalized intensity data is mapped to a distribution of the reflectivity data for deriving the n and k map of the slider surface.

Figure 8:
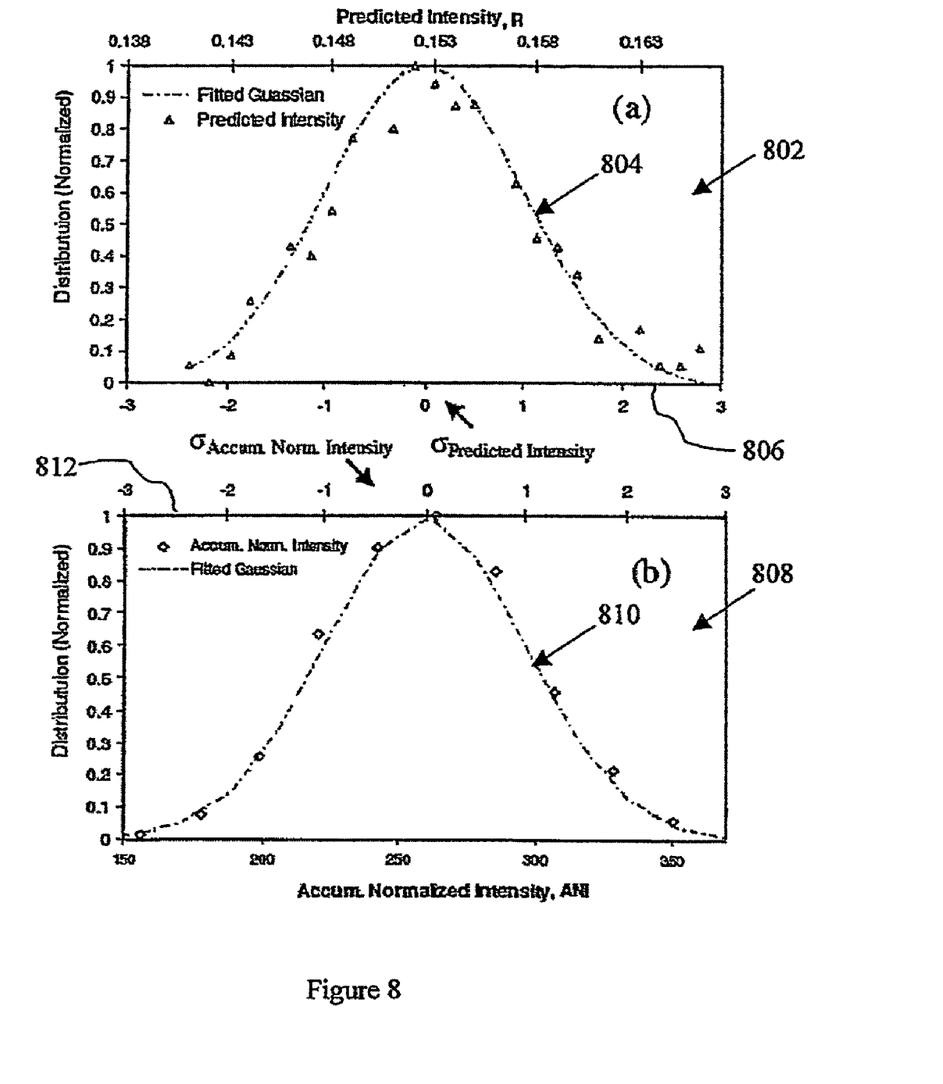
FIG. 8(a) is a graph showing a fitted Gaussian plot based on intensity reflectivity R plotted against its normalised distribution.
FIG. 8(b) is a graph showing another fitted Gaussian plot based on accumulated normalised intensity ANI plotted against its normalised distribution.

FIG. 8 (*a*) is a graph 802 showing a fitted Gaussian plot 804 based on intensity reflectivity R plotted against its normalised distribution. The R values are as obtained at step 704 of FIG. 7. Based on the fitted Gaussian plot 804, an axis of statistical deviation (ie. $\sigma_{Predicted\ Intensity}$) 806 is obtained.

FIG. 8 (*b*) is a graph 808 showing another fed Gaussian plot 810 based on accumulated normalised intensity ANI plotted against its normalised distribution. The ANI values are as obtained at step 702 of FIG. 7. Based on the fitted Gaussian plot 808, an axis of statistical deviation (ie. $\sigma_{ANI}$) 812 is obtained.

Based on the statistical deviation axes 806, 812, the fitted Gaussian plot 804 of R can be mapped to the fitted Gaussian plot 810 of ANI (see step 706 (FIG. 7)).

Figure 9:
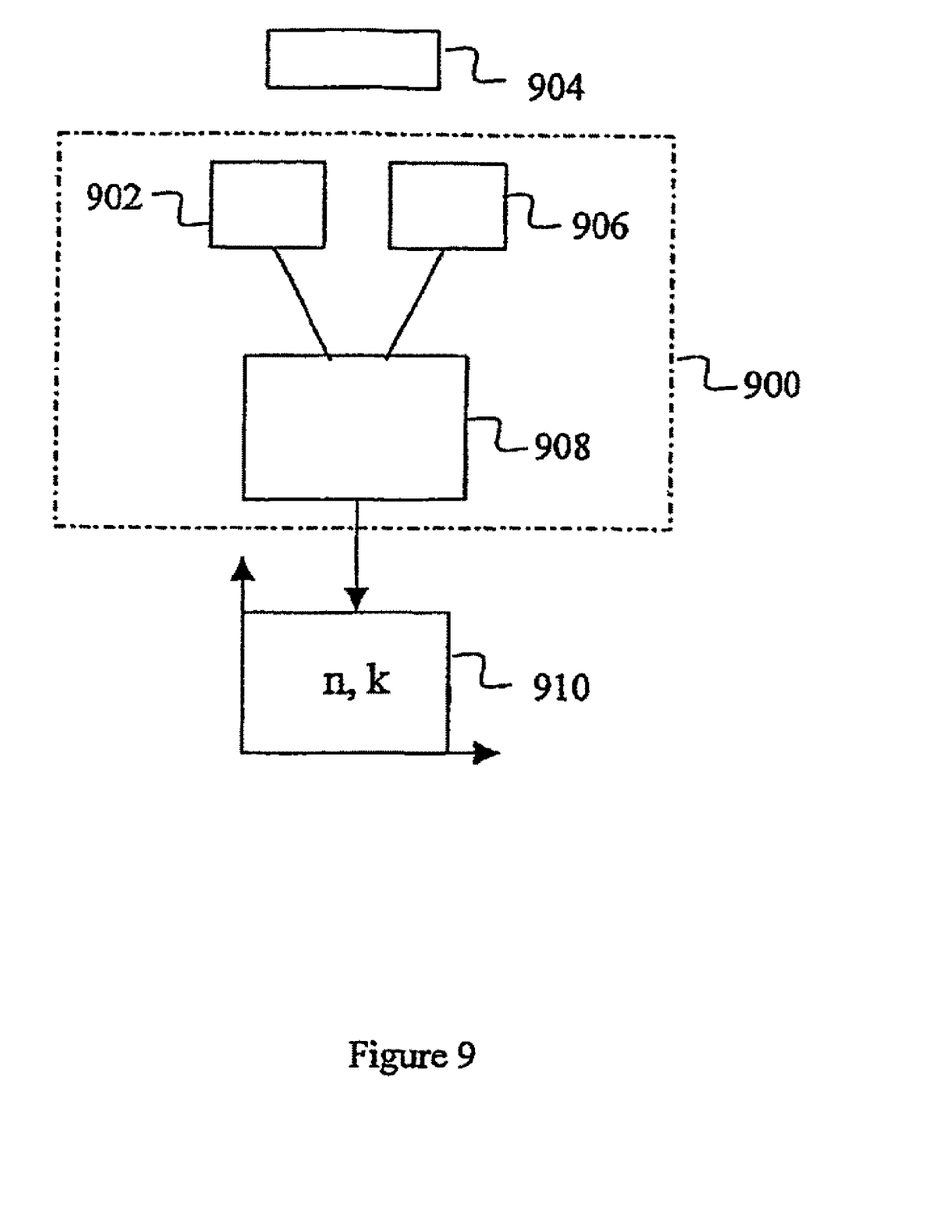
FIG. 9 is a schematic drawing of a system for obtaining an n and k map of a slider surface.

FIG. 9 is a schematic drawing of a system 900 for obtaining a refractive index (n) and extinction coefficient (k) map of a slider surface. The system comprises a processor 902 for processing an image of the slider surface 904 to obtain spatially resolved normalized intensity data of the slider surface 904. The system further comprises a measurement unit 906 for measuring n and k values of the slider surface 904 at different areas of the slider surface to obtain reflectivity data of the slider surface 904. A mapping unit 908 for mapping a distribution of the normalized intensity data to a distribution of the reflectivity data is coupled to the processor 902 and the measurement unit 906, for deriving the n and k map 910 of the slider surface 902.

In addition, the system 900 and/or the processor 902 can be attached to a FH tester for providing in-situ n, k values on demand for each FH measurement spot.

Figure 10:
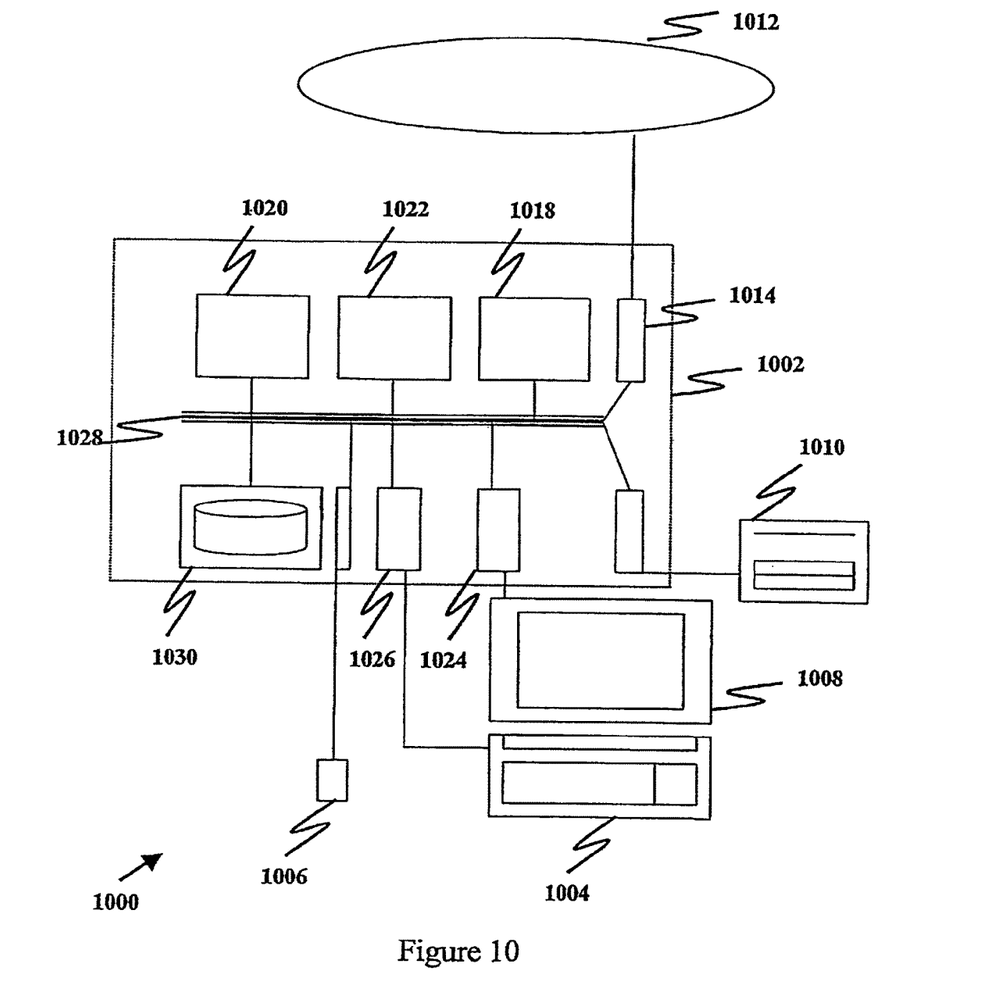
FIG. 10 is a schematic diagram illustrating a computer system for implementing the example implementation.

The example implementation can be implemented on a computer system 1000, schematically shown in FIG. 10. It may be implemented as software, such as a computer program being executed within the computer system 1000, and instructing the computer system 1000 to execute the example implementation.

The computer system 1000 comprises a computer module 1002, input modules such as a keyboard 1004 and mouse 1006 and a plurality of output devices such as a display 1008, and printer 1010.

The computer module 1002 is connected to a computer network 1012 via a suitable transceiver device 1014, to enable access to e.g. the Internet or other network systems such as Local Area Network (LAN) or Wide Area Network (WAN).

The computer module 1002 in the example includes a processor 1018, a Random Access Memory (RAM) 1020 and a Read Only Memory (ROM) 1022. The computer module 1002 also includes a number of Input/Output (I/O) interfaces, for example I/O interface 1024 to the display 1008, and I/O interface 1026 to the keyboard 1004.

The components of the computer module 1002 typically communicate via an interconnected bus 1028 and in a manner known to the person skilled in the relevant art.

The application program is typically supplied to the user of the computer system 1000 encoded on a data storage medium such as a CD-ROM or floppy disk and read utilising a corresponding data storage medium drive of a data storage device 1030. The application program is read and controlled in its execution by the processor 1018. Intermediate storage of program data maybe accomplished using RAM 1020.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method for obtaining a refractive index (n) and extinction coefficient (k) map of a slider surface, the method comprising the steps of:
   processing an image of the slider surface to obtain spatially resolved normalized intensity data of the slider surface;
   measuring n and k values of the slider surface at different areas of the slider surface to obtain reflectivity data of the slider surface;
   mapping a distribution of the normalized intensity data to a distribution of the reflectivity data for deriving the n and k map of the slider surface.

2. The method as claimed in claim 1, further comprising determining a corresponding reflectivity value for each data point of the spatially resolved normalized intensity data from the mapping of the distributions, deriving a corresponding n value from the corresponding reflectivity value, and calculating a corresponding k value from the corresponding reflectivity and n values.

3. The method as claimed in claim 2, wherein the corresponding n value is derived from the corresponding reflectivity value based on an empirical relationship.

4. The method as claimed in claim 3, wherein the empirical relationship is based on an empirical linear curve.

5. The method as claimed in claim 1, wherein processing the image comprises removing height related information utilizing a plane-fit processing.

6. The method as claimed in claim 5, wherein the plane-fit processing comprises determining a plane having a minimum sum of squared distances in a normal direction of the plane.

7. The method as claimed in claim 1, wherein the processing of the image comprises removing illumination condition related information utilizing a normalization processing.

8. The method as claimed in claim 7, wherein the normalization processing comprises dividing the image into tiles and the normalized intensity data is based on normalizing maximum and minimum pixel values in each tile.

9. The method as claimed in claim 1, wherein the n and k values are measured utilizing ellipsometry.

10. The method as claimed in claim 1, wherein the image comprises a charge-coupled device (CCD) image.

11. The method as claimed in claim 1, further comprising performing a fly-height measurement of the slider utilizing the n and k map of the slider surface.

12. A system for obtaining a refractive index (n) and extinction coefficient (k) map of a slider surface, the system comprising:
    means for processing an image of the slider surface to obtain spatially resolved normalized intensity data of the slider surface;
    means for measuring n and k values of the slider surface at different areas of the slider surface to obtain reflectivity data of the slider surface
    means for mapping a distribution of the normalized intensity data to a distribution of the reflectivity data for deriving the n and k map of the slider surface.

13. The system as claimed in claim 12, wherein the means for mapping determines a corresponding reflectivity value for each data point of the spatially resolved normalized intensity data from the mapping of the distributions, derives a corresponding n value from the corresponding reflectivity value, and calculates a corresponding k value from the corresponding reflectivity and n values.

14. The system as claimed in claim 13, wherein the corresponding n value is derived from the corresponding reflectivity value based on an empirical relationship.

15. The system as claimed in claim 14, wherein the empirical relationship is based on an empirical linear curve.

16. The system as claimed in claim 12, wherein the means for processing removes height related information by utilizing a plane-fit processing.

17. The system as claimed in claim 16, wherein the plane-fit processing comprises determining a plane having a minimum sum of squared distances in a normal direction of the plane.

18. The system as claimed in claim 12, wherein the means for processing removes illumination condition related information by utilizing a normalization processing.

19. The system as claimed in claim 18, wherein the normalization processing comprises dividing the image into tiles and the normalized intensity data is based on normalizing maximum and minimum pixel values in each tile.

20. The system as claimed in claim 12, wherein the n and k values are measured by utilizing ellipsometry.

21. The system as claimed in claim 12, wherein the image comprises a charge-coupled device (CCD) image.

22. The system as claimed in claim 12, further comprising means for performing a fly-height measurement of the slider utilizing the n and k map of the slider surface.

23. A data storage medium having computer code means stored thereon for instructing a computer to execute a method for obtaining a refractive index (n) and extinction coefficient (k) map of a slider surface, the method comprising the steps of:
    processing an image of the slider surface to obtain spatially resolved normalized intensity data of the slider surface;
    measuring n and k values of the slider surface at different areas of the slider surface to obtain reflectivity data of the slider surface;
    mapping a distribution of the normalized intensity data to a distribution of the reflectivity data for deriving the n and k map of the slider surface.

* * * * *